United States Patent [19]

Harris et al.

[11] Patent Number: 5,074,137
[45] Date of Patent: Dec. 24, 1991

[54] PROGRAMMABLE ATMOSPHERIC STABILIZER

[76] Inventors: Ronald J. Harris, 2645 Nutmeg; Steven E. Hamilton, 2637 Nutmeg, both of Simi Valley, Calif. 93063

[21] Appl. No.: 652,312

[22] Filed: Feb. 6, 1991

Related U.S. Application Data

[63] Continuation of Ser. No. 301,604, Jan. 24, 1989, abandoned.

[51] Int. Cl.$^5$ .......................................... G01N 31/00
[52] U.S. Cl. ................................................ 73/31.02
[58] Field of Search ............... 73/31.01, 31.02, 432.1; 340/506, 511, 517, 521, 588, 584, 628, 632–634

[56] References Cited

U.S. PATENT DOCUMENTS

| | | | |
|---|---|---|---|
| 3,826,180 | 7/1974 | Hayashi . | |
| 4,122,761 | 10/1978 | Westin et al. . | |
| 4,308,911 | 1/1982 | Mandl | 165/11.1 |
| 4,335,379 | 6/1982 | Martin | 340/634 |
| 4,338,526 | 7/1982 | Martin et al. . | |
| 4,390,869 | 6/1983 | Christen et al. | 340/521 |
| 4,464,651 | 8/1984 | Duhame . | |
| 4,526,028 | 7/1985 | Hubner . | |
| 4,536,747 | 8/1985 | Jensen | 340/521 |
| 4,592,967 | 6/1986 | Komatsu et al. | 340/634 |
| 4,622,538 | 11/1986 | Whynacht et al. | 340/506 |
| 4,630,038 | 12/1986 | Jordan . | |
| 4,673,920 | 6/1987 | Ferguson et al. | 340/506 |
| 4,699,519 | 10/1987 | Persson | 340/584 |
| 4,831,361 | 5/1989 | Kimura | 340/511 |

OTHER PUBLICATIONS

Sierra Monitor Corporation, reprinted from Microelectronic Manufacturing and Testing, Feb. 1986, "Gas Risk Management—A Safer Approach to Monitoring for Hazardous Gases" by Robert E. Dunkle.

*Primary Examiner*—Robert Raevis
*Attorney, Agent, or Firm*—Christie, Parker & Hale

[57] ABSTRACT

A programmable atmospheric stabilizer uses one or more sensors for detecting the condition of potentially hazardous materials within a container or some other enclosed atmosphere. The sensors connect to a first threshold detector which activates a first order correcting device when the sensor detects a first order hazard. The sensor also connects to a second threshold detector which activates a second correcting device when the sensor detects a second order hazard. The first correcting device may be a fan, and the second correcting device may include an alarm. A variety of different sensors can be connected to one monitoring unit and a variety of different correcting devices can be activated by the monitoring unit. Each monitor can be connected to a central location where the sensed levels and the activity of the correcting devices can be monitored. The threshold levels at which each of the correcting devices are activated can be adjusted independently and when the monitors are coupled to a central control unit the correcting devices can be controlled from the central location. The monitor acts independently and is suitable for different applications including hazardous storage containers, manufacturing plants, parking structures, and office buildings.

29 Claims, 4 Drawing Sheets

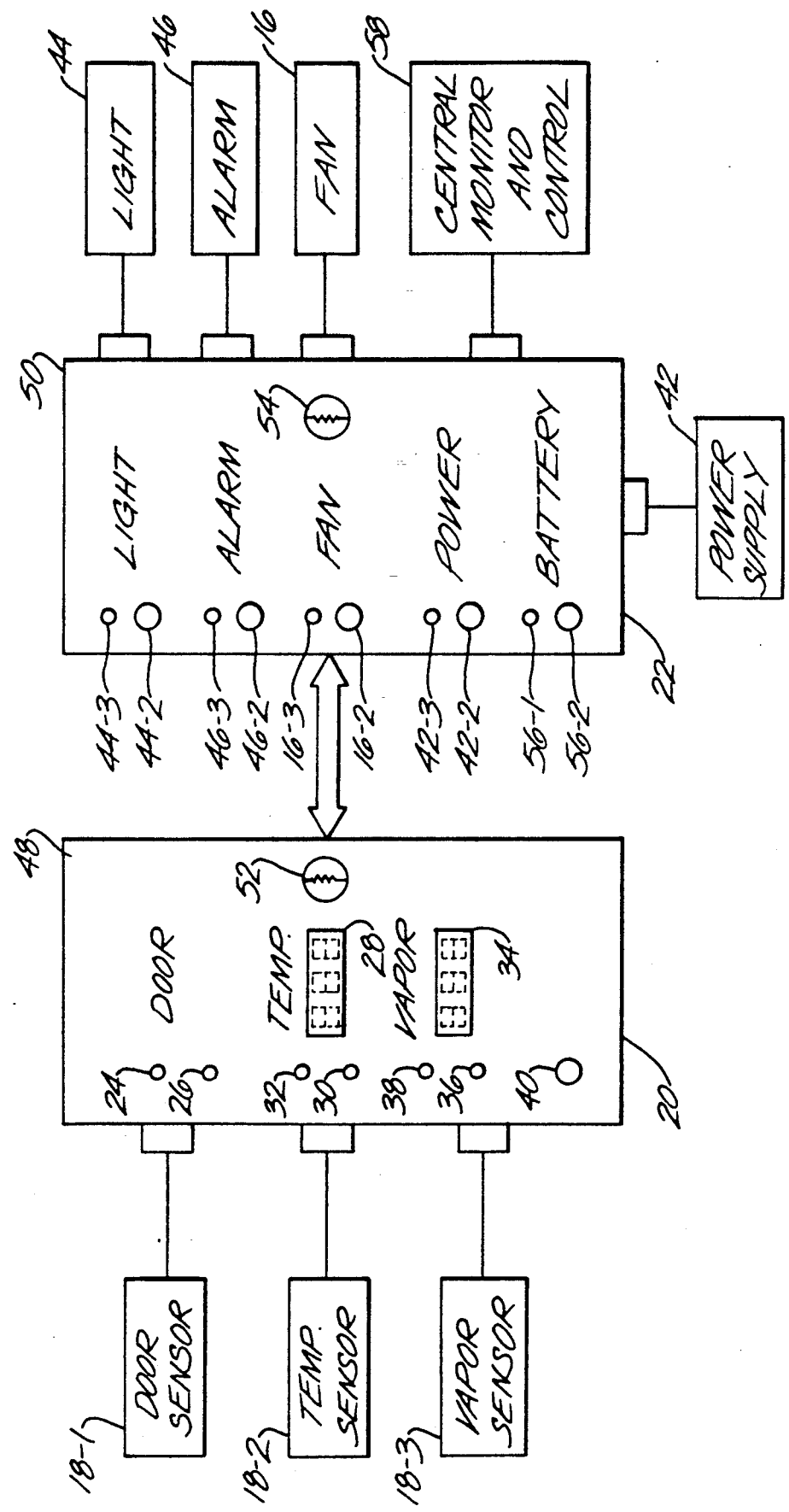

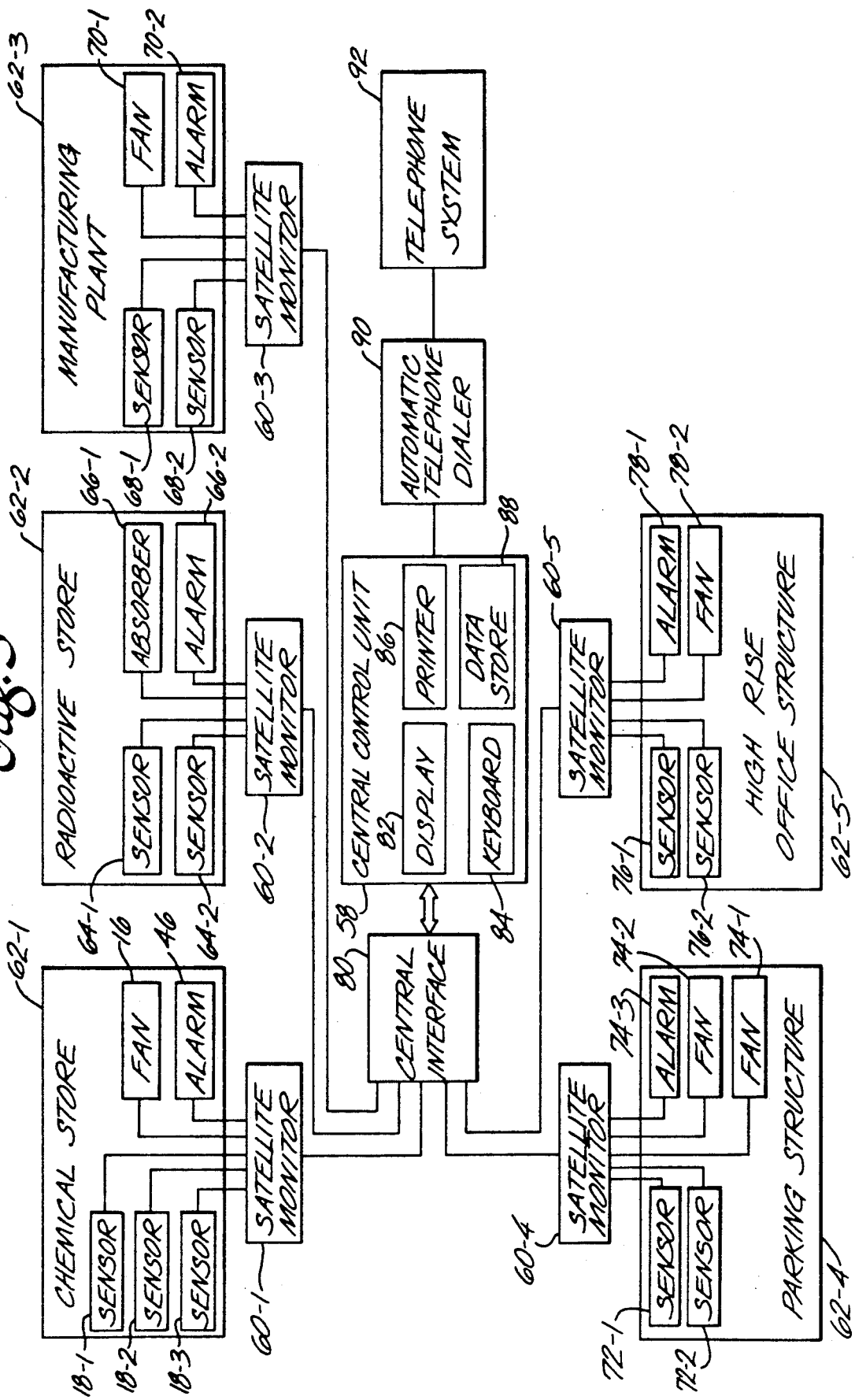

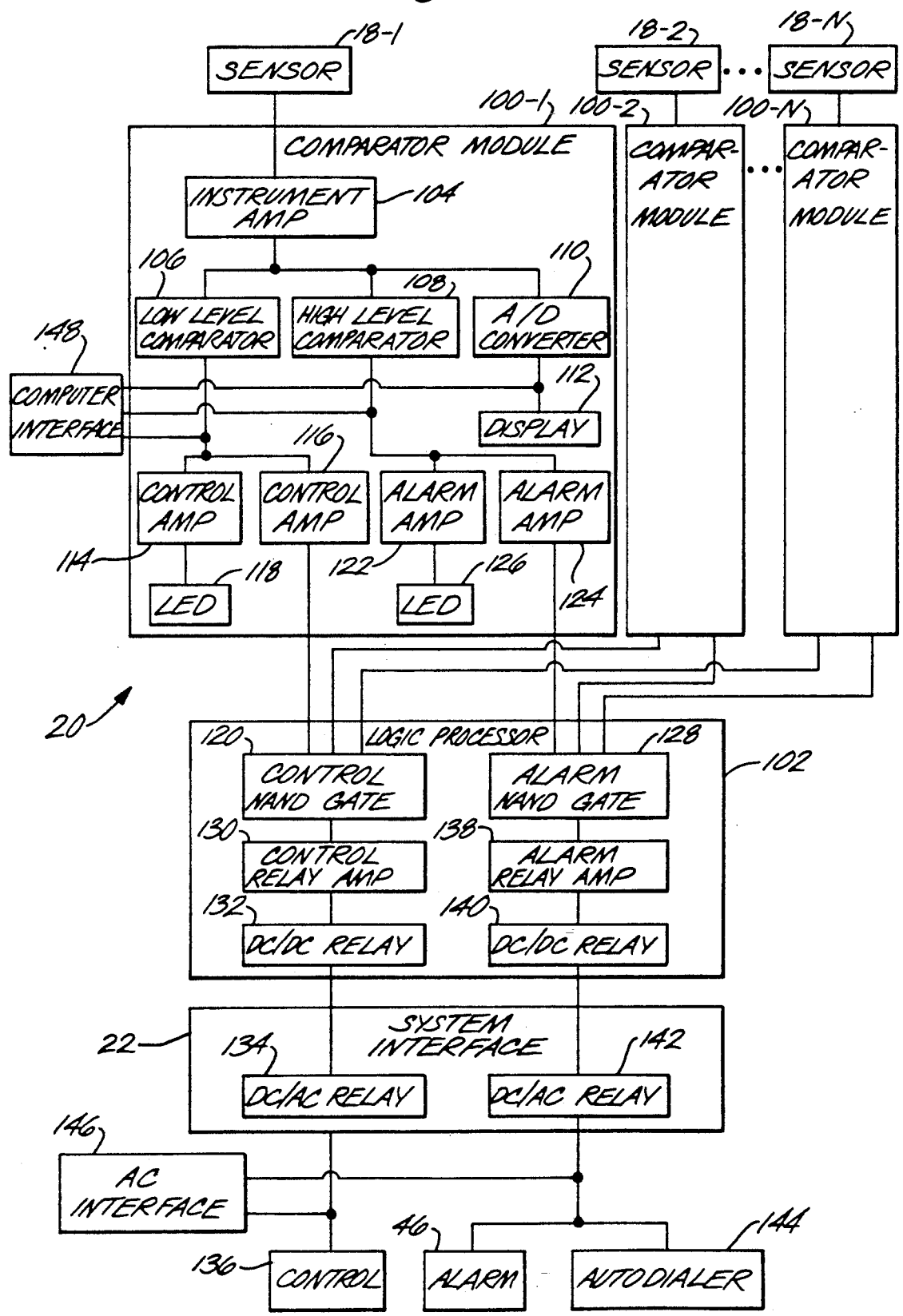

PROGRAMMABLE ATMOSPHERIC STABILIZER

CROSS-REFERENCE TO RELATED APPLICATIONS

This is a continuation of application Ser. No. 301,604, filed Jan. 24, 1989, now abandoned.

FIELD OF THE INVENTION

The present invention pertains to the field of environment management and more particularly to a flexible programmable atmospheric stabilizer for correcting hazardous conditions in a variety of atmospheres and situations.

BACKGROUND OF THE INVENTION

Hazardous materials, whether they are raw materials or waste byproducts, are essential to many industries. These industries must inventory or stockpile a significant amount of these materials in order to satisfy their daily manufacturing needs or disposal schedules. Unfortunately, any significant collection of hazardous materials, whether they are toxic, radioactive, explosive, corrosive or highly reactive in some other way pose a threat to the environment and to people nearby. Active chemicals may be leaked into the surrounding atmosphere and cause injuries to nearby workers or residents. Chemical fires are often hard to extinguish and can cause significant damage. Radioactive leaks and toxic dumping can have severe long-term effects and often attract vast amounts of public attention even when the risk of injury is not great. Society, in general, has become increasingly aware of the risk of injury and, as a result, industries are being required to contain or reduce the risks.

Industries are developing new techniques for storing hazardous, toxic and radioactive materials partly due to regulatory mandate and partly on their own initiative. Instead of simply dumping toxic chemicals or other industrial wastes in a spare corner of the plant site, industries are being required to storehouse these materials until they can be shipped to an approved dumping site. Instead of stockpiling chemical reagents and other dangerous materials in a fenced back lot, industries are being required to contain these materials in sealed steel or cement containers to prevent them from leaking into the air or from igniting spontaneously.

These new techniques create new problems. Hazardous chemicals, be they radioactive or chemically active, are typically stored in steel or plastic drums which are in turn stockpiled in steel or cement containers or buildings. Locked away in their sealed buildings, the individual barrels are difficult to monitor. Leaks, or chemical changes inside the containers can result in hazardous conditions for workers who must enter the building or in explosions which can endanger nearby people and structures.

Hazardous materials also pose these same risks when they are not in storage. Laboratories, manufacturing plants, and even parking and office structures use or are exposed to hazardous materials which can endanger people and structures. While the problems posed by hazardous materials outside of storage containers are not new, society's concern for these risks is increasing.

Presently there exist a variety of sensors which may be adapted to determine whether a hazardous condition exists within a container or other environment. However, no system exists for determining the level of the hazard and automatically taking a corrective measure to alleviate the hazard or alternatively warning of a hazard which cannot be reliably alleviated.

Sensing and recording devices are available in a variety of configurations. U.S. Pat. No. 4,526,028 to Hubner, for example, shows a system capable of measuring, displaying, and recording a variety of atmospheric parameters; for example, temperature, humidity, air pressure and noxious gas concentration. If the concentration of noxious gases becomes too high, an alarm will sound. Typical household smoke detectors similarly measure the presence of smoke and sound an alarm if the concentration exceeds a predefined threshold. In large buildings, smoke levels are detected at a variety of satellite locations to sound a control alarm. These systems, however, do nothing to alleviate the smoke hazard or the presence of noxious gases.

U.S. Pat. No. 3,826,180 to Hayashi shows a ventilation fan system with a smoke detector speed control. This device includes a circuit to activate the fan when a smoke or gas from a cooking range is detected to ventilate a kitchen. U.S. Pat. No. 4,338,526 to Martin and U.S. Pat. No. 4,404,651 to Duhame show gas and smoke detectors which open a garage door when the level exceeds a predefined threshold. The garage door opener is integrated into a home security system. U.S. Pat. No. 4,308,911 to Mandl shows a system which integrates smoke detector, security and air conditioning systems using a computer. The Duhame system simply operates an alarm in response to excess smoke, however.

SUMMARY OF THE INVENTION

Notwithstanding the teachings of the prior art, there remains a need for a flexible programmable atmospheric stabilizer which can be applied to a variety of situations and yet be networked together to a central monitoring and control location. In one embodiment, the invention comprises a flexible hazardous condition monitoring and correcting device with an input port to receive a signal, a threshold detector connected to the input port for determining whether the signal at the input port exceeds a threshold level, and an output port connected to the threshold detector for connection to a correcting device. The output port transmits a signal activating the correcting device when the sensor input exceeds the threshold. The threshold level is adjustable so that the threshold level corresponds to a hazardous condition at the sensor.

The device may also have a second threshold detector for sensing whether the signal at the input port exceeds a second higher threshold level and a second output port connected to the second threshold detector for transmitting a signal activating a second correcting device when the sensor input exceeds the second threshold. The second threshold level is also adjustable. The second threshold corresponds to a hazardous condition which cannot normally be alleviated by the first correcting device. The first correcting device may be a fan and the second correcting device an alarm for signalling that the hazardous condition cannot normally be alleviated by the fan.

In another embodiment, the invention is a storage system which includes a closed container for storing potentially hazardous materials. A sensor detects the condition of the materials within the container and generates a signal in response thereto. A correcting device is associated with the container for alleviating hazardous conditions within the container and a control circuit is coupled between the correcting device and the sensor for operating the correcting device in response to the signal generated by the sensor in order to alleviate hazardous conditions within the container.

The hazardous materials are preferably canisters containing potentially dangerous substances. A hazardous condition occurs if the dangerous substances escape from the canister. The sensor accordingly comprises a probe for detecting the presence of the substances outside the canisters but within the container. The sensor may measure the concentration of a chosen class of substances within the container or a temperature within the container. Typical substances detected by the sensor are carbon monoxide, chlorine, ammonia, hydrocarbons, sulfur compounds and oxygen. Typical correcting devices include fans, water sprays, chemical sprays, and alarms.

The container may also have a closeable door to allow access to the interior of the container and a sensor associated with the door for detecting whether the door is closed. The control circuit would then include means for activating an alarm when the door is not closed.

In another embodiment, the invention is a programmable environment monitor and control system comprising a plurality of satellite monitors. Each satellite monitor has an input port for receiving signals from a sensor indicating the presence of a hazardous condition, an output port for transmitting a correcting signal to a correcting device when a hazardous condition is indicated, and an interface connected to the input and output ports. The system also has a central control unit connected to the interface of each satellite monitor with a display for indicating the signals transmitted at each output port and a control panel for controlling the correct distribution signals transmitted at each output port.

The system also has at least one control circuit for generating a correction signal at the output port of each monitor when the corresponding input port receives a signal indicating a hazardous condition. When the input port receives a variable signal, the control circuit may comprise an adjustable threshold detector for detecting when the signal at the input port exceeds an adjustable threshold and a correction signal generator for providing a correction signal to a corresponding output port when the input port receives a signal which exceeds the threshold.

The control circuit may also comprise a second adjustable threshold detector for detecting when the input signal exceeds a second adjustable threshold and a second correction signal generated for providing a second correction signal to a corresponding output port when the input port receives a signal which exceeds the second threshold. The control circuit may be associated with the central control unit or with one or more of the individual satellite monitors. The central control unit may have a switching circuit for independently controlling the signal generated at the output port of a monitor. It may have means for adjusting the first and second thresholds, and it may have means for recording and displaying signals received from a satellite monitor.

BRIEF DESCRIPTION OF THE DRAWINGS

FIG. 2 is a block diagram of one embodiment of the control system and interface of the present invention showing a variety of inputs and outputs.

FIG. 3 is a block diagram of an industrial plant incorporating the present invention for centralized monitor and control of a variety of environments.

FIG. 4 is a block diagram of circuitry used to implement the control system and interface of FIG. 3.

DETAILED DESCRIPTION

Figure 1:
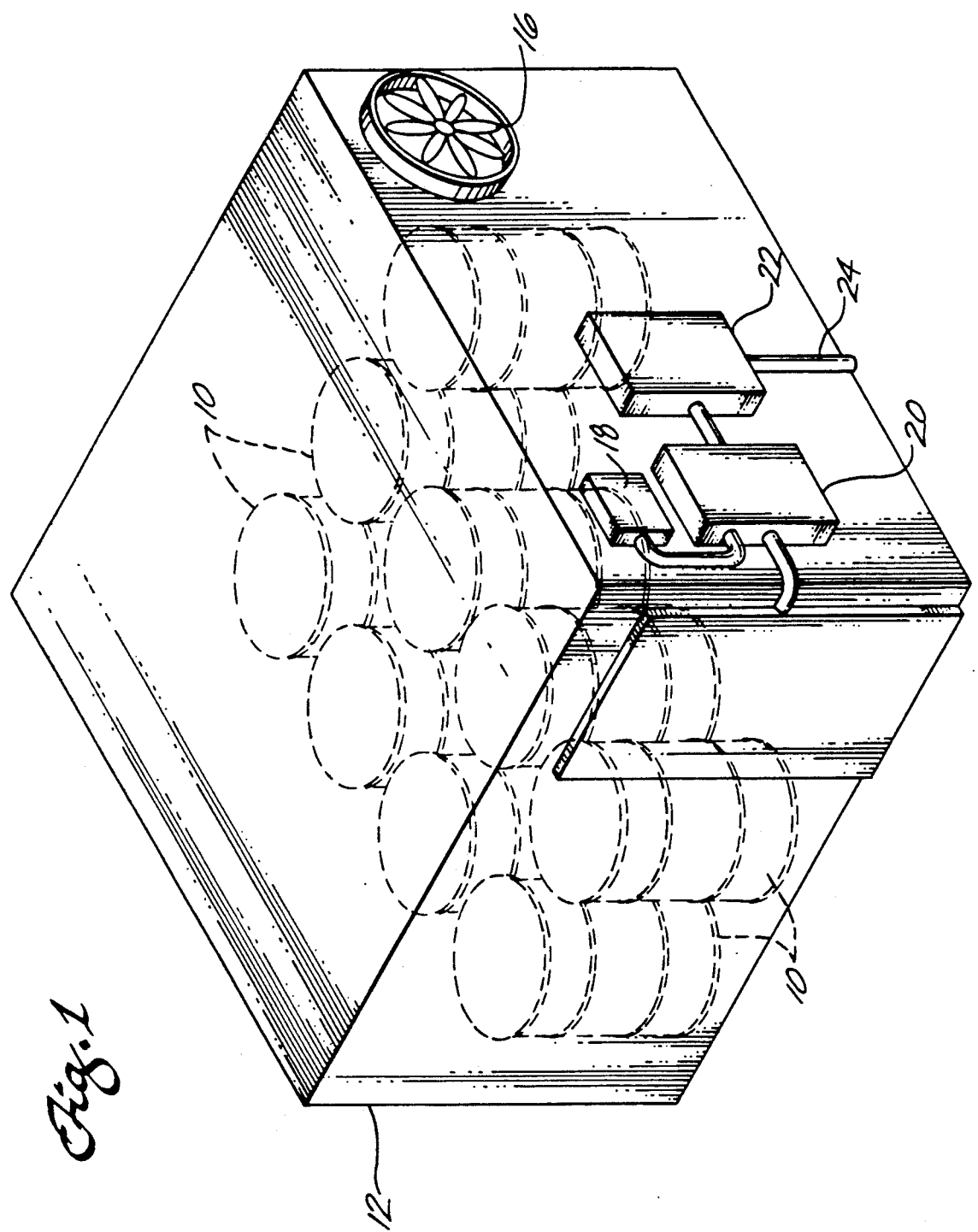
FIG. 1 is a perspective view of a storage system according to the present invention showing a container equipped with sensors, a correcting device and a control circuit.

FIG. 1 shows a typical storage system for potentially hazardous materials according to the present invention. The materials may be toxic, radioactive, explosive, corrosive or they may present a potential hazard in some other way. To prevent the potential hazards, the materials are each contained in separate canisters 10. Fifty-five gallon steel drums are often used but other canisters may also be used depending on the materials to be stored. To further reduce any hazards brought on by the canisters, they are placed in a container 12 which is typically steel or concrete. The container is designed to contain any leaks or small explosions that may occur in or between the canisters. Thus even if the canisters become hazardous, the hazard is kept within the container.

A door 14 permits access to the canisters so that they can be removed, replaced or repaired. At least one fan 16 is provided on one wall of the building in order to vent gases leaking from the canisters out of the container. Venting these gases can prevent fires, explosions and the like until the leaking canister can be repaired. The fan may vent the air and gases directly into the outside environment as shown in FIG. 1 or the gases may first be blown by the fan to an air washing device to prevent the gases from being released to the outside. The storage system also uses a set of sensors 18 enclosed in a housing which is coupled to a control system 20. The sensors may be arranged to detect overall conditions in the container or a single condition at a specific location. They may also be adapted to detect conditions in a particular canister. The control system is in turn connected to an interface 22 as more fully explained with reference to FIG. 4. A main power line 24 provides the power necessary to drive the storage system including the sensors 18, control system 20, interface 22, and fan 16.

FIG. 2 shows the control system 20 and interface 22 and their interconnections in block diagram form in a typical embodiment suitable for the storage system of FIG. 1. The control system receives signals from three different sensors. Three sensors are shown in this example. However, more or fewer sensors may be used depending on the environment to be monitored. A door sensor 18-1 indicates whether the door is opened or closed by providing either of two voltage signals, a high voltage signal for indicating the door is closed and a lower voltage signal for indicating the door is opened. The temperature sensor 18-2 provides an analog voltage signal indicative of the temperature within the container. Any one of the variety of analog temperature sensors known in the art can be used. A vapor sensor 18-3 provides an analog voltage signal indicative of the concentration of vapor within the container 12. Any of a variety of vapor sensors available on the market may be used. The vapor sensor is chosen to indicate whether one of the canisters is leaking. The correct sensor to be chosen depends on what is stored in the canisters. For example, if the canisters were used to store hydrochloric acid, a chlorine sensor could be used to indicate if hydrochloric acid was escaping from the canister. If a leak cannot be readily detected with a vapor sensor, some other type of sensor, for example a liquid sensor or geiger counter, may be used instead.

Each of these sensors enters a separate circuit which interprets the signal from the sensor. The circuitry is described in more detail with reference to FIG. 4. If the door sensor indicates that the door is open, a red light 24 on the front panel 48 of the control system 20 will be illuminated indicating a potential hazard or security risk. If the door is closed, a green light 26 will be illuminated indicating that there is no risk (i.e., that the container is in a safe condition). The temperature sensor signal is interpreted in a comparator circuit. The temperature is displayed on a light-emitting diode (LED) display 28 and compared to two threshold levels. These thresholds, as well as the thresholds for the vapor sensor, may be programmed to suit as explained below with reference to FIG. 4. If the temperature is below the first threshold, then a green light 30 on the control system's front panel will be illuminated indicating a safe condition. If the temperature exceeds the first threshold, a red light 32 will be illuminated on the control system panel indicating a hazardous condition which requires attention.

The analog input from the vapor sensor 18-3 is treated similarly. The vapor level is displayed on the control panel LED display 34 in parts per million or some similar units. A green light 36 indicates a safe condition. A red light 38 indicates that a hazard exists. When a red light is lit, the degree and nature of the risk can be determined from the corresponding LED display, and from the fan and alarm status as discussed below. A single LED 40 indicates that power is being supplied to the control system 20. Two threshold detection levels have been chosen for simplicity and because two levels are adequate for most applications. However, three or more threshold levels could be used where a different response occurs when each threshold is exceeded.

The control system 20 is dependent upon and communicates with a system interface 22. The system interface is connected to a main system power supply 42 and distributes power to the different parts of the storage container system including an interior light array 44 for illuminating the interior of the container, an alarm 46 for warning of hazardous conditions, and the fan 16 which is used to vent reactive chlorine, for example, from the container to prevent deadly concentrations. As mentioned above, vapors vented from the container may first be washed before being released to the environment. Each of these systems is controlled by a relay operated by a switch on the front panel of the system interface. The relays are more fully described below with reference to FIG. 4.

The light relay is controlled by a light switch 44-2 on the interface panel and the status of the light is indicated by an LED 44-3. An alarm relay can be controlled by a switch 46-2 and the status of the alarm is indicated by an LED 46-3. The fan relay can be controlled by a switch on the exterior panel 16-2 and the status of the fan is indicated by an LED 16-3. Power to the complete system can be turned on or off by operating the power switch 42-2. When power is supplied to the system, an LED 42-3 is illuminated. When a red light is activated on the control system, the level of the hazard can be determined by checking the lights on the system interface. If only the fan has been activated, indicated by the fan light 16-3, the risk is a low level one exceeding only the first threshold. If the alarm is also activated, indicated by the alarm light 46-3, then the risk is a high level one exceeding the second threshold.

The system interface 22 is also provided with a back-up system. An LED 56-1 indicates that the batteries are sufficiently charged and a switch 56-2 is provided so that the batteries can be manually switched in and out. The system interface is constructed so that when power from the power supply 42 is cut off, the back-up battery system automatically switches in to provide power to the container system. Any type of automatic relay system can be used for this feature using techniques well known in the art.

The front panels 48, 50 of the control system and system interface respectively can be held closed with a lock 52, 54 respectively to prevent unauthorized access to the interior of the control system and system interface. Any of the switches for the light, alarm and power can be provided behind the front panel 50 of the system interface to prevent unauthorized access to the switches. Similarly, unauthorized adjustment of the threshold levels for the temperature and vapor sensor can be restricted with the lock 52 on the front panel 48 of the control system.

The system interface is coupled to the control system 20 and provides the low voltage direct current (DC) necessary to drive the various sensors, comparator systems, logic processors and displays of the control system 20. The control system 20 in turn supplies signals to the system interface which drive relays to engage the alarm and fan. If the first threshold for either the temperature or vapor is exceeded, the control system 20 transmits a signal to the system interface which switches on the fan 16 in order to alleviate the hazardous condition detected. In the case of a container filled with hydrochloric acid canisters, the fan would vent chlorine which had leaked out of the canisters into a chlorine wash system to prevent deadly concentration from forming within the container itself. If the temperature or vapor level exceeds the second threshold, a signal is transmitted from the control system 20 to the system interface 22 to also activate the alarm relay. The alarm indicates that danger is imminent and it is unlikely that the fan will be able to alleviate the hazardous condition.

All of the high power electric components are contained within the system interface box 22, while most of the low power DC circuitry is contained within the control system box 20. This arrangement is preferred for isolating the larger relays and transformers of the system interface box from the more delicate electronics of the control system box, enhancing the safety of the total atmospheric stabilizer system. However, the system may be provided in more or fewer discrete boxes or with no boxes at all. The container system as described can operate self-sufficiently to monitor the condition of the container, automatically correct for hazardous conditions, and warn of extreme hazards. The system can be adapted to a variety of container or building atmospheres. Instead of vapor level of chlorine, the vapor level of other chemicals could be detected, for example, carbon monoxide, carbon dioxide, ammonia, hydrocarbons, oxides of nitrogen, hydrogen chloride, hydrogen fluoride, sulfurs, chlorines, oxygen, etc. In the alternative, a liquid sensor could be provided to detect the presence of spilled liquids on the floor of the container.

Humidity and barometric pressure could also be measured. Any combination of these sensors may be combined as multiple inputs to a single control system 20 so that an excessive reading by any one of the sensors would activate the fan or alarm. The sensor inputs could also be gated so that a combination of high sensor readings is required to activate the fan or alarm. For example, excessive humidity together with an excessive temperature could be required before the alarm and fan would be activated.

The outputs of the system interface 22 can also be varied to suit different situations. Many different correcting devices may be used. Instead of a fan, a dehumidifier, a cooling system or a neutralizing chemical spray, for example, could be used. When the sensor inputs exceed the second threshold, a stronger corrective action could be activated, in addition to an alarm. For example, fire retardant foams or stronger neutralizing sprays may be used. It is preferred that the alarm system be maintained, however, to alert of any dangers. The system of FIG. 2 can be used independently as a self-contained system. Periodic checks ensure that the necessary maintenance of the container and its contents is performed when the sensed conditions are consistently too high. Regular servicing of the atmospheric stabilizer may be provided to ensure that the sensors are all properly calibrated and the back-up batteries are charged.

The system of FIG. 2 is also a great convenience to those who must enter the container 12 to remove, repair or replace storage canisters 10. Before opening the container door, the conditions inside the container can be checked. If only the green lights 24, 32, 38, 40, 42-3 are lit, then the container is reasonably safe. However, the LED displays 28, 34 may also be checked. If the sensed levels indicated on the digital displays 28, 34 are high, extra precautions may be used. If any of the sensor warning lamps 32, 38, 16-3, 46-3, are lit, extreme caution would be indicated. The digital displays 28, 34 indicate the seriousness of the condition. If a moderate risk is indicated but the risk is not great enough to actuate the fan, the fan may be activated manually using the switch 16-2 on the control panel. The lights and alarm can similarly be conveniently operated. In addition, if the power light 40 for the sensor is off, the container should be checked before the door is opened. After the container has been entered and exited, the system also indicates through the door lamps 24, 26 whether the door has been closed, securing the container.

The system of FIG. 2 may also be provided without the threshold detection and automatic relay features described above. In this case, the temperature and vapor levels would still be monitored, however, if a hazardous condition were detected as indicated on one of the digital displays, then an operator would have the obligation of activating the fan or alarm using the switches provided 16-2, 46-2. This arrangement would require frequent monitoring by the operator in order to manually correct for any potentially hazardous conditions before the hazard fully develops. The system would, however, provide most of the same benefits discussed above to those who must enter the container 10 to remove, repair or replace storage canisters 12.

Finally, the system of FIG. 2 may also be coupled to a central monitoring and control unit 58 so that the status of a plurality of containers may be monitored from one central location. Such a system is indicated in FIG. 3.

FIG. 3 shows an adaptation of the present invention which employs several satellite monitors 60. Each monitor includes a control system 20 and system interface 22 similar to that described with respect to FIG. 2. Each satellite monitor may be coupled to one or a plurality of different sensor inputs. Two and three sensor inputs are shown in FIG. 3 as examples, however, more or fewer may be used. In addition, each monitor may actuate one or a plurality of correcting devices, for example a fan and an alarm. Two and three correcting devices are shown in FIG. 3 as examples, however, more or fewer may be used. Each monitor is coupled to a central control unit 58. The first satellite monitor is associated with a chemical storage container similar to that of FIG. 1. As explained with respect to FIG. 2, a plurality of sensors are used to detect hazardous conditions and a fan and alarm are used to respond to these conditions.

The second satellite monitor 60-2 is adapted to monitor the conditions within a radioactive material storage container 62-2. The radioactive storage container 62-2 has a configuration similar to the storage container of FIG. 1, however, the first sensor 64-1 is a door sensor and the second sensor 64-2 would be a geiger counter. In the event that the geiger counter detects more than a first threshold level of radiation, radiation absorbing rods 66-1 could be introduced into the storage container. In the event that the radioactivity exceeds a second threshold, an alarm 66-2 would be sounded.

The third satellite monitor 62-3 is associated with a manufacturing plant 62-3. Again a plurality of sensors 68-1, 68-2 would be used to detect whether toxins in the atmosphere surrounding any hazardous materials used in the manufacturing plant exceed a certain predefined threshold concentration. If the first threshold were exceeded, a fan 70-1 is activated to vent the hazardous materials from the work place and if a second threshold is exceeded, an alarm 70-2 is sounded to recommend stronger action or evacuation. As discussed above with respect to FIG. 2, a variety of chemicals can be detected and a variety of responses can be employed when the threshold concentration is exceeded. The system may also be adapted for use as a fire prevention device so that either one or both of the sensors 68-1, 68-2 is a smoke detector and either one or both of the corrective devices 70-1, 70-2 is a sprinkler system.

A fourth satellite monitor 60-4 is associated with a parking structure 62-4. Sensors in the parking structure 72-1, 72-2 detect levels of car exhaust. Carbon monoxide, hydrocarbons or oxides of nitrogen may be measured. One sensor detects levels in one area of the structure and the other detects levels in another area. In response to excess exhaust levels detected by the first sensor, a first correcting device, a fan 74-1, is activated. If, after the fan is activated, the exhaust levels exceed a second threshold level, an alarm 74-3 is activated. If the second sensor detects excess exhaust levels, the second fan 74-2 is activated. The second fan vents an area near the second sensor. The alarm 74-3 is also sounded if the second fan fails to correct the situation at the second sensor.

Applying the satellite monitor 60-4 to a parking structure yields several advantages not obtained in other applications. Most multi-level parking structures require fans in order to remove vehicle emissions from inside the parking structure so that it is safe for humans to park their cars. The fans must be large enough to provide adequate ventilation under peak use periods. For example, in a typical office structure traffic is heaviest in the mornings from 8:00 to 9:00, around lunch time, and in the afternoon from around 5:00 to 6:00. During other periods of the day, however, there is relatively less activity and late at night there is often little or no activity at all in the parking structure. During these off periods, the large fans consume expensive power but provide no benefit. The fans can be controlled with a timer. However, the timer does not take into consideration any variations in parking structure use, for example weekend conferences. As a result, many parking structure fans are operated full time. This is expensive, and wasteful.

The satellite monitor 60-4 regulates the fans directly according to exhaust levels in the parking structure. The fans are therefore operated only when necessary. Heavy traffic during a special event poses no risk to parking structure users and the fans are not used excessively during holidays and evening hours. Separate sensor and fan circuits may be provided for each level or area of the parking structure so that fans are only used in the areas where they are required. The other additional utility provided by the satellite monitor is that if excessive levels of carbon monoxide are present in the garage and cannot be alleviated, an alarm is sounded which might warn parking lot users to avoid entering the parking structure.

The entire garage can be monitored and controlled from the central control unit. One or more satellite monitors and one or more fans may be used. A variety of sensors can be coupled to each satellite monitor for more reliable operation of the fan. The satellite monitor 60-4 in the garage is also a type of security indicator. If exhaust is detected in a secured portion of the garage, that indicates an unauthorized vehicle in the secured part of the garage. Multiple sensors in different locations within the secured portion of the garage can more precisely indicate the location of the unauthorized vehicle on the central control unit. For additional security, the exhaust gas sensors can be combined with motion detectors, infrared sensors, or some other type of sensor. As stated above, multiple sensors may be connected to one satellite monitor or multiple satellite monitors may be used.

The fifth satellite monitor 60-5 is associated with a high rise office structure. The first sensor 76-1 is designed to detect smoke within the office structure and the second sensor 76-2 is designed to detect toxic chemicals in the office structure. If the output of either of the sensors exceed a first threshold, a fan is activated to vent the building of smoke or toxic chemicals. Preferably the fan is associated with an elevator shaft and the satellite monitor causes the elevators to stop and fans in the elevator shafts to switch on, venting the smoke and toxic chemicals out through the elevator shafts. Many of the deaths caused by large building fires are caused not by burns but by inhalation of toxic chemicals generated by the fire and carried in its smoke. Applying a satellite monitor to a high rise office structure allows the toxic chemicals to be vented from the building, potentially saving many of the lives of those who are not exposed to flame directly. If the sensor output exceeds a second threshold, an alarm 78-1 is sounded to warn of the danger. All of the satellite monitors are coupled to a central interface 80 which in turn couples to a central control and monitoring unit 58. The central control unit includes a display 82, a keyboard 84, a printer 86, and a data store 88. The printer and data store may be replaced with a simple chart plotting recorder to save cost. Each satellite monitor 60 transmits information concerning the sensor inputs and the status of the correcting devices. The central control unit displays this information. The information can also be stored in the data store and reports can be printed on the printer. Using the keyboard 84, the correcting devices can be operated from the central control unit overriding the threshold level settings at any particular satellite monitor. The central control unit allows every condition monitored by a satellite monitor 60 to be monitored from a single central location. It also allows any alarms or corrections to be controlled from one central location. In addition, using a single central control unit, any hazardous condition shown on the display 82 can be quickly located and identified by maintenance and rescue crews. The central control unit is coupled to an automatic telephone dialer 90 to call plant managers, fire departments, environmental monitoring agencies, and the like, when particular hazards are detected. The automatic telephone dialer connects into a conventional telephone system 92 and plays a specific recorded message unique to each satellite monitor identifying the particular hazard over the telephone. The recorded message identifies the location of the hazard and the types of chemicals involved. A unique message can be provided for each sensor or for discrete groups of sensors using techniques well known in the art.

FIG. 4 is a block diagram of the electrical configuration of the control system 20 and system interface 22 and their connections to the associated equipment. A plurality of sensors 18-1 to 18-N are coupled one to one to a plurality of comparator modules 100-1 to 100-N. The comparator modules are all coupled to a single logic processor 102. The comparator modules and the logic processor together make up the control system 20. The logic processor is in turn coupled to the system interface 22 which connects to the various correcting devices. Each sensor 18 is driven by a reference voltage regulator (not shown) to provide a voltage signal to an instrument amplifier 104 as is well known in the art. The voltage of the input signal from the sensor varies with the sensor detection response. Virtually all commonly available sensors provide an analog voltage output. However, if a current signal or some other type of signal were produced, the signal could be converted using well known techniques.

The instrument amplifier provides a voltage signal corresponding to the sensor output to a low level comparator 106, a high level comparator 108, and an analog to digital converter 110. The analog to digital converter provides a series of digital outputs in order to drive an LED display 112, for example, one of the LED displays 28, 34 or FIG. 3. The low level comparator compares the signal from the instrument amplifier to a preselected reference voltage. If the voltage from the instrument amplifier 104 is higher than the predetermined first threshold voltage, then the low level comparator 106 sends a low level voltage to each of two control amplifiers 114, 116. The low level output corresponds to a digital "zero". The threshold voltage may be programmed and calibrated using well known techniques. For example, the comparator may contain a voltage divider for setting the threshold voltage made up of variable resistors. On receiving the digital signal from the comparator, the first control amplifier 114 drives an LED 118 indicating that the first threshold has been exceeded. The second control amplifier 116 provides a low level input to a NAND gate 120 in the logic processor 102. If the voltage from the instrument amplifier is lower than the voltage from the low level comparator 106, then the comparator provides a high digital one signal to each of the control amplifiers. The LED 118 is turned off and a high signal is asserted at the NAND gate 120.

Similarly, the high level comparator 108 compares the voltage from the input instrument amplifier to a second higher threshold voltage. This voltage may also be programmed and calibrated. If the voltage from the instrument amplifier exceeds the second higher voltage, then the high level comparator transmits a low voltage or zero digit to each of two alarm amplifiers 122, 124. The first alarm amplifier 122 then drives a light emitting diode 126 which indicates on the front panel of the control system that the particular sensor exceeds the second threshold level. This condition corresponds to a risk which probably cannot be alleviated using the correcting device driven by the low level comparator. The alarm amplifier 124 asserts a low level input to the NAND gate 128. If the instrument amplifier output voltage is lower than the second threshold level, then the high level comparator 108 asserts a high voltage or digital one at the alarm amplifiers 122, 124 shutting off the LED 126 and providing a high signal at the NAND gate 128.

Each of the other comparator modules 100-2 to 100-N perform in a similar way. The sensors 18-2 to 18-N may sense for the same condition in a different area of the container or they may sense different substances. The control amplifier outputs of all of the comparator modules 100-2 to 100-N are combined at the control NAND gate 120. If all the signals from the control amplifiers are high, the NAND gate produces no output. This indicates that the conditions detected by all of the sensors are below the predetermined threshold levels for each sensor and no hazardous condition exists. Accordingly, the NAND gate produces no output and no correcting device is engaged. If, however, any one of the control amplifier outputs drops to a low state or digital zero, the NAND gate produces a high output.

The high output from the NAND gate 120 is amplified in a relay amplifier 130 which provides a signal to a DC to DC relay 132. The amplified DC signal is provided from the control system 20 to the system interface 22 where it is coupled to a DC to AC relay. The AC current switched in by the relay is then applied to a control or correcting device 136 which, as mentioned above, may be a fan, a dehumidifier, an air conditioner, a neutralizing sprayer, or any number of other AC driven correcting devices.

The alarm NAND gate 128 works similarly. All of the alarm amplifier outputs from the comparator modules 100 are routed to a single alarm NAND gate 128. As long as the inputs from the alarm amplifiers remain in a high state, the alarm NAND gate 128 produces no output signal. However, whenever the output of any alarm amplifier drops below the second predetermined threshold, the NAND gate transmits a high signal to the alarm relay amplifier 138. This indicates that a hazardous condition exists which the correcting device 136 is unlikely to alleviate. The alarm relay amplifier 138 is coupled to a DC/DC relay and then to the system interface 22 and a DC/AC relay 142. This relay provides current to drive an alarm 46 and an autodialer 144. The alarm may be an alarm signal to an operator, a local audible alarm on the container or a larger alarm for a whole plant. The autodialer may be preprogrammed to alert the fire department that a fire is imminent at the particular container being monitored or as mentioned above, it may be programmed to alert a plant manager, environmental monitoring agency, etc. Any autodialer available on the market may be used. The alarm and autodialer are provided as examples. As mentioned above, a large number of different devices could be driven by the AC relay 142 including more effective correcting devices.

In the present embodiment, it is contemplated that one logic processor could receive signals from up to 10 comparator modules. All of the sensors drive the same DC to AC relays 134, 142. To achieve a different kind of response to a particular sensor, a different logic processor arrangement is required. The specific arrangement of gates and sensor inputs may be varied to suit different installations. For example, two comparator outputs from different sources could be combined at a NOR gate and then sent to the corresponding NAND gate 120, 128 so that both sensors must indicate a hazardous condition before a control device would be activated. Certain sensors may be wired to activate any one or several correcting devices.

The control circuit including the low level comparators 106, second control amp 116, control NAND gate 120, control relay amp 130 and relays 132, 134 can be arranged so that the control device response varies according to the risk. Using a fan, for example, fan speed can increase as the level detected at the sensor increases. Alternatively, the alarm loop can be used to drive a second fan so that when the second threshold is exceeded more ventilation is applied. The comparator module can also be constructed to use more than two comparators. As the sensor response increases a series of corrective devices can be engaged as each threshold is exceeded culminating, for example, in an alarm. Alternatively, each comparator could send a signal to a single fan relay to drive the one fan at progressively higher speeds. Any number of fans or other correcting devices may be coupled to the same DC/AC relay. A variety of correcting devices have been suggested above in conjunction with other embodiments.

FIG. 2 shows switches which provide a manual override of the fan and alarm. These switches may be connected to the fan and alarm using techniques well known in the art. For example, a separate AC switch between the device and the corresponding DC/AC relay can be provided. The power supply, battery backup, and light controls shown in FIG. 3 are connected in a conventional manner. The circuitry of FIG. 4 can be connected to a central monitor unit in at least two different ways. The simplest method is to use an AC interface 146. This interface taps into the wires between the AC relays 134, 142 and their corresponding correcting devices 136, 146, 144. Conventional AC wiring connects to a central panel using this approach. A number of satellite monitors can be connected to a central panel using a technique similar to the approach shown in FIG. 4. The panel can provide a display indicating which of the relays in the system have been activated as well as an override feature allowing the control device 136, the alarm 46, or the autodialer 144 to be activated from the central location. Using a separate indicator for each relay and multiple satellite monitor system, the operator can determine whether a hazardous condition has been detected at any of the satellite monitors and whether the condition corresponds to the first threshold level of the control NAND gate at that monitor or to the high threshold level of the alarm NAND gate at that monitor. In the case of a low level hazardous condition, he can notify the appropriate service or maintenance crew to investigate the monitored container to permanently repair the condition or, in the case of a high level hazardous condition, more serious measures could be taken, for example, evacuation or fire department intervention. Allowing the operator to switch on or off the control device 136 or alarm 46 and autodialer 144 provides an additional measure of control.

Alternatively, the computer interface 148 can be used. In FIG. 4, the computer interface connects to the outputs of the low level comparator 106, high level comparator 108, and A/D converter 110 from each of the comparator modules 100-1 to 100-N at each of the satellite monitors. Using this information, the operator at the central location is informed, by the A/D converter and associated display, specifically what level is being sensed by each sensor in the system and, by the outputs of the comparators, whether that sensor output exceeds the first and second thresholds of the system and accordingly whether a correcting device or alarm had been sounded. The operator asserts an overriding manual control to the logic processor through means grounding either the low level comparator output or high level comparator output to simulate a low level output at either comparator. Grounding the comparator output would provide a low state or digital zero at the respective NAND gate which, as explained above, would cause the relays to switch in the corresponding control device.

The computer interface 148 is better suited to the central control unit 58 of FIG. 3 in that it provides a large amount of information. The status of every sensor in the system is monitored, and control can be asserted over any control device. Storing the outputs of each of the sensors gives an overall history of the entire plant. This history can be reviewed to anticipate maintenance needs. Money is saved because maintenance can be consolidated and planned in advance. However, it is more difficult to transmit the low voltage and current signals produced by the comparators and the A/D converter. If a large number of monitors are to be coupled to a central control unit or if the distances are very great, the signals must usually be amplified several times. Preferably the signals are serialized and transmitted over some common bus system to a central interface 80 where they would be deserialized and retransmitted to the central control unit. The comparatively high voltage AC interface can be constructed simply over rather long distances using conventional AC wiring.

The programmable atmospheric stabilizer of the present invention including the control system 20 and interface 22 can be easily adapted to a large number of different systems from a simple single sensor, fan and alarm device to a complicated multiple monitor, central control unit where each monitor receives information from a large number of sensors and regulates different control devices accordingly. Each control system and system interface combination operates independently of the other with its own backup battery supply but can also be controlled from a remote centralized location. In a large plant this can be a great advantage. Hazards which otherwise may not be identifiable can be located quickly and conveniently from the central control unit. A reference guide at that control location can determine what sorts of materials are involved before rescue or maintenance crews arrive. By recording the outputs of the many sensors in a data store or using a printer. Every monitored condition can be examined to preplan maintenance and repair work long before the situation becomes hazardous. The battery backup is particularly valuable when tires and corrosives present the risk of a power failure. The battery may be arranged to power only the circuitry and alarms or the entire container.

The present invention is a flexible system which can be adapted to take many forms. The specific examples provided in this description are meant as examples only. It will be understood by those skilled in the art that a variety of variations and modifications could be made without departing from the spirit and scope of the invention. By presenting only the embodiments shown above, the inventor does not intend to abandon any of those variations and modifications.

What is claimed is:

1. A programmable environment monitor and control system comprising:
    a plurality of satellite monitors, each monitor having an input port for receiving signals from a sensor and an output port for transmitting a correction signal to a correcting device; and
    a central control unit in communication with each monitor having a display for displaying a representation of the signal received at each monitor input port and a control panel for controlling the correction signal transmitted at each monitor output port.

2. The system of claim 1 wherein at least one monitor comprises a control circuit for generation a correction signal in response to the input port signal and providing the correction signal to the corresponding output port of the monitor independent of the central control unit.

3. The system of claim 1 wherein the input port of at least one monitor is adapted to receive a variable signal, and wherein said at least one monitor comprises a control circuit having:
    an adjustable threshold detector for detecting when the signal received at the input port exceeds an adjustable threshold; and
    a correction signal generator for providing a correction signal to the corresponding output port when the input port receives a signal which exceeds the threshold.

4. The system of claim 3 wherein the central control unit comprises means for adjusting the threshold.

5. The system of claim 3 wherein the central control unit comprises means for receiving the correction signal.

6. The system of claim 3 wherein the control circuit also comprises a second adjustable threshold detector for detecting when the input signal exceeds a second adjustable threshold and a second correction signal generator for providing a second correction signal to the output port when the input port receives a signal which exceeds the second threshold.

7. The system of claim 6 wherein the central control unit comprises means for adjusting the first threshold and means for adjusting the second threshold.

8. The system of claim 6 wherein the central control unit comprises means for receiving the first correction signal and means for receiving the second correction signal.

9. The system of claim 1 wherein the central control unit comprises means for transmitting a correction signal to the output port of a monitor independent of the corresponding input port signal.

10. The system of claim 1 wherein the central control unit comprises a control circuit for generating a correction signal for transmission to the output port of a monitor in response to the signal received at the input port of said monitor.

11. The system of claim 1 wherein the control unit comprises means for storing information received from the monitors.

12. The system of claim 11 wherein the storing means comprises a printer.

13. The system of claim 1 wherein the control unit comprises means for transmitting a signal indicating the presence of a hazardous condition to a telephone system in response to the signal received at an input port.

14. The system of claim 1 wherein the control unit comprises means for transmitting a signal indicating the presence of a hazardous condition to a telephone system in response to a correction signal.

15. The system of claim 1 also comprising at least one sensor connected to the input port of each monitor for providing a signal indicating the status of each monitored condition.

16. The system of claim 15 wherein the at least one sensor is adapted to detect carbon monoxide.

17. The system of claim 15 wherein the at least one sensor is adapted to detect chlorine.

18. The system of claim 15 wherein the at least one sensor is adapted to detect ammonia.

19. The system of claim 15 wherein the at least one sensor is adapted to detect temperature.

20. The system of claim 15 wherein the at least one sensor is adapted to detect hydrocarbons.

21. The system of claim 1 wherein at least one satellite monitor further comprises additional input ports for receiving signals from additional sensors.

22. A programmable environment monitor and control system comprising:

a plurality of satellite monitors, each monitor having an input port for receiving signals from a sensor, a control circuit for interpreting the sensor signal and generating a correction signal in response thereto, an output port for transmitting the correction signal, and an interface in communication with the control circuit; and a central control unit in communication with the interface of each monitor, the control unit having a display for displaying a representation of each sensor signal and a control panel for controlling the correction signal transmitted by each output port.

23. The system of claim 22 wherein the control circuit comprises an adjustable threshold detector for detecting when the sensor signal exceeds an adjustable threshold and generating the correction signal in response to the detection.

24. The system of claim 23 wherein the control unit comprises means for adjusting the threshold.

25. The system of claim 23 wherein the control circuit comprises a second adjustable threshold detector for detecting when the sensor signal exceeds a second adjustable threshold and generating a second correction signal in response to the second detection.

26. The system of claim 25 wherein the control circuit comprises means for adjusting the first threshold and means for adjusting the second threshold.

27. The system of claim 1 wherein each monitor comprises means actuable manually at the monitor for causing a correction signal to be transmitted to a correction device.

28. The system of claim 22 wherein each monitor comprises a display for displaying an indication of the sensor signal.

29. The system of claim 22 wherein each monitor comprises means actuable manually at the monitor for causing a correction signal to be transmitted.

* * * * *

UNITED STATES PATENT AND TRADEMARK OFFICE
CERTIFICATE OF CORRECTION

PATENT NO. : 5,074,137

DATED : December 24, 1991

INVENTOR(S) : Ronald J. Harris; Steven E. Hamilton

It is certified that error appears in the above-identified patent and that said Letters Patent is hereby corrected as shown below:

In the Claims:

Column 14, line 31, change "generation" to
-- generating --.

Column 14, line 56, before "output" insert
-- corresponding --.

Signed and Sealed this

Fourth Day of May, 1993

Attest:

MICHAEL K. KIRK

Attesting Officer

Acting Commissioner of Patents and Trademarks